(12) United States Patent
Heesch

(10) Patent No.: US 12,343,478 B2
(45) Date of Patent: Jul. 1, 2025

(54) ANESTHETIC DISPENSER WITH MIXING UNIT AND ANESTHETIC TANK AND PROCESS USING ANESTHETIC DISPENSER

(71) Applicant: Drägerwerk AG & Co. KGaA, Lübeck (DE)

(72) Inventor: Ralf Heesch, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 554 days.

(21) Appl. No.: 17/846,229

(22) Filed: Jun. 22, 2022

(65) Prior Publication Data

US 2022/0409846 A1 Dec. 29, 2022

(30) Foreign Application Priority Data

Jun. 24, 2021 (DE) ...................... 10 2021 116 392.7

(51) Int. Cl.
*A61M 16/18* (2006.01)
*A61M 16/10* (2006.01)

(52) U.S. Cl.
CPC ..... *A61M 16/18* (2013.01); *A61M 2016/1035* (2013.01)

(58) Field of Classification Search
CPC ............ A61M 16/0891; A61M 16/009; A61M 16/01; A61M 16/104; A61M 16/18–186; A61M 2016/1035
See application file for complete search history.

(56) References Cited

U.S. PATENT DOCUMENTS

| | | | |
|---|---|---|---|
| 8,356,596 B2 | 1/2013 | Brandt et al. | |
| 10,406,313 B2 | 9/2019 | Danielsen | |
| 2013/0087146 A1* | 4/2013 | Callaghan | A61M 16/0063 128/204.21 |
| 2019/0099581 A1* | 4/2019 | Kuzelka | A61M 16/024 |
| 2019/0117921 A1 | 4/2019 | Bender, II et al. | |
| 2021/0093826 A1* | 4/2021 | Lacey | A61M 16/1005 |
| 2021/0290887 A1 | 9/2021 | Zechlin et al. | |

FOREIGN PATENT DOCUMENTS

| | | |
|---|---|---|
| DE | 102008057180 B3 | 4/2010 |
| EP | 2170447 B1 | 7/2017 |
| WO | 2005056093 A1 | 6/2005 |
| WO | 2008151668 A1 | 12/2008 |
| WO | 2020030408 A1 | 2/2020 |
| WO | 2020167737 A1 | 8/2020 |

* cited by examiner

*Primary Examiner* — Rachel T Sippel
(74) *Attorney, Agent, or Firm* — McGlew and Tuttle, P.C.

(57) ABSTRACT

An anesthetic dispenser (100) includes an anesthetic tank (7) and a mixing unit (9) that mixes an anesthetic from the anesthetic tank with a carrier gas. Liquid anesthetic (Nm) can be refilled into the anesthetic tank through a refill opening (6). In one operating mode, a specified operating pressure is maintained. A closure (16) is moveable from a closed position via an intermediate position to an open position and closes the refill opening in both the closed position and the intermediate position. When the closure is moved from the closed position to the intermediate position, a transition time period elapses. A position sensor (22) detects the event that the closure has been moved out of the closed position. In response to this detection, pressure in the anesthetic tank is lowered during the transition period to a refill pressure that is still above ambient pressure. The closure is then opened.

13 Claims, 6 Drawing Sheets

ANESTHETIC DISPENSER WITH MIXING UNIT AND ANESTHETIC TANK AND PROCESS USING ANESTHETIC DISPENSER

CROSS REFERENCE TO RELATED APPLICATIONS

This application claims the benefit of priority under 35 U.S.C. § 119 of German Application 10 2021 116 392.7, filed Jun. 24, 2021, the entire contents of which are incorporated herein by reference.

TECHNICAL FIELD

The invention relates to an anesthetic dispenser with a mixing unit and with an anesthetic tank. In the mixing unit, an anesthetic from the anesthetic tank is mixed with a carrier gas, and thereby a gas mixture comprising the anesthetic is produced. Furthermore, the invention relates to a process for generating such a gas mixture using such an anesthetic dispenser.

TECHNICAL BACKGROUND

Such an anesthetic dispenser is often used to generate a gaseous anesthetic using liquid anesthetic and to supply a patient with a gas mixture comprising the carrier gas and gaseous anesthetic. Using this gas mixture, the patient is temporarily anesthetized.

Various such anesthetic dispensers have become known. EP 2 170 447 B1 and U.S. Pat. No. 10,406,313 B2 describe an anesthetic vaporizer 100 with an anesthetic tank (receptacle 107 for receiving a liquid anesthetic 106). A protective member in the form of a lid 90 closes a refill port 18 through which anesthetic 106 can be refilled into the anesthetic tank 107 and which comprises a valve (valve system having a filling valve 101). A level sensor 102 measures the current level in the anesthetic tank 107. A pressure sensor 104 measures the pressure in the anesthetic tank 107. A first sensor (93, 74) determines whether the closure 90 is open or closed. A second sensor 78 determines whether a bottle of anesthetic is inserted into the refill opening 18. An injector valve 111 injects anesthetic into a mixing chamber 112, and carrier gas is introduced into measurement chamber 112 through an inlet port 113. In order to be able to supply a patient with anesthetic even when anesthetic is being refilled into tank 107, anesthetic is temporarily stored in a buffer reservoir (secondary reservoir 22).

Arrangements to supply liquid anesthetic to an anesthetic dispenser and to refill anesthetic into an anesthetic tank are also described in U.S. Pat. No. 2019/0117921 A1, in WO 2020/030408 A1, in WO 2020/167737 A1, in WO 2008/151668 A1 and in WO 2005/056093 A1.

SUMMARY

The invention is based on an object of providing an anesthetic dispenser and a process for generating (producing) a gas mixture comprising an anesthetic and a carrier gas, which are mechanically simpler in construction than known anesthetic dispensers and processes while maintaining similar operational safety.

The task is solved by an anesthetic dispenser with the features of the invention and by a process with the features of the invention. Advantageous embodiments are disclosed herein. Advantageous embodiments of the anesthetic dispenser are, as far as useful, also advantageous embodiments of the process and vice versa.

The anesthetic dispenser according to the invention comprises
- a mixing (feed, injection) unit,
- an anesthetic tank with a refill opening (port),
- a closure (shutter) for the refill opening,
- an anesthetic line leading (guiding) from the anesthetic tank to the mixing unit,
- a controllable pressure increasing (boosting) unit and a controllable pressure reducing (lowering) unit,
- a pressure sensor,
- a position sensor for the closure and
- a signal processing control unit.

The process according to the invention is carried out using such an anesthetic dispenser.

The anesthetic dispenser is configured to provide a gas mixture suitable for anesthetizing a patient. This gas mixture comprises at least one gaseous anesthetic, optionally a plurality of anesthetics, and a carrier gas, wherein the carrier gas comprises oxygen. The carrier gas may be a mixture of a plurality of gaseous components.

An anesthetic can flow from the anesthetic tank through the anesthetic line to the mixing unit. The term "line" refers to a rigid or flexible fluid delivery unit, in particular a smooth hose, a corrugated hose or a tube.

The gas mixture is generated in the mixing unit by mixing the anesthetic or at least one anesthetic, preferably any anesthetic supplied, with the carrier gas, the anesthetic preferably being fed into a stream of the carrier gas, for example by injecting or vaporizing or evaporating the anesthetic into the carrier gas stream.

The anesthetic dispenser can be operated in an operating mode. When operated in the operating mode, at least one anesthetic, preferably a liquid anesthetic, is supplied from the anesthetic tank to the mixing unit, and the anesthetic or at least one anesthetic supplied is mixed with the carrier gas, preferably fed into the carrier gas.

According to the invention, the anesthetic or each anesthetic used is mixed with the carrier gas, preferably injected into a stream of carrier gas. In one embodiment, the carrier gas is mixed together from at least two carrier gas components, and the anesthetic is mixed with this gas mixture from the carrier gas components. In another embodiment, breathing air or a mixture of breathing air with another gas flowing to the patient is used as the carrier gas. Optionally, the breathing air acting as the carrier gas, or as a part of the carrier gas, flows in a ventilation circuit from a medical device, in particular a ventilator, to the patient and back to the medical device. Into this carrier gas comprising breathing air, the anesthetic or an anesthetic is injected. It is also possible that a carrier gas, which has preferably been generated from at least two carrier gas components, is fed into a stream of breathing air at a first feed point and the anesthetic is fed in at a spatially spaced second feed point.

The pressure sensor is capable of measuring a measure of the actual pressure in the anesthetic tank and generating a signal for the measured pressure. The control unit is capable of
- to receive and process the pressure signal,
- triggering and preferentially terminating an increase of the pressure in the anesthetic tank by the control unit controlling (actuating) the pressure increasing unit, and
- triggering a reduction in the pressure in the anesthetic tank and preferably terminating a reduction in pressure by the control unit controlling (actuating) the pressure reduction unit.

The pressure increasing unit and the pressure reducing unit can be realized by the same component, which is operable in different modes, or by different components.

The actual pressure in the anesthetic tank is at a specified (predetermined or preset) operating pressure or above this operating pressure in the operating mode. This operating pressure is above the ambient pressure and can vary over time. The ambient pressure is the actual air pressure in the vicinity of the anesthetic tank and is specified or measured. The control unit receives a value for the specified or measured ambient pressure.

The control unit causes the actual pressure in the anesthetic tank to be equal to or above the operating pressure in the operating mode. The operating pressure is above the ambient pressure. In one embodiment, a target operating pressure is specified to be maintained in the operating mode. This target operating pressure may be constant over time or may vary over time. The control unit performs automatic control with the goal that the actual pressure in the anesthetic tank is equal to the specified target operating pressure. In one embodiment, the control unit performs unilateral control with the aim of ensuring that the actual pressure is equal to or greater than the operating pressure.

The positive pressure in the anesthetic tank relative to the ambient pressure helps to deliver the anesthetic to the mixing unit. The positive pressure saves the need for a pump to deliver the anesthetic. In addition, the positive pressure reduces the risk of the usually undesirable event of gaseous anesthetic or carrier gas or other gas or gas mixture flowing from the mixing unit back into the anesthetic tank. This can lead in particular to gas bubbles in a liquid.

It is possible that at least two different anesthetics are conveyed to the mixing unit and mixed successively or simultaneously with the carrier gas, and therefore the generated gas mixture comprises at least two different anesthetics. It is also possible that a gas with at least one anesthetic and a further gas component, for example breathing air or pure oxygen, is conveyed to the mixing unit and a further anesthetic is added there. In the following, "(one) anesthetic" is used for simplification, and this is understood to mean "at least one anesthetic".

The anesthetic in the anesthetic tank is used up (consumed), especially because at least one patient is anesthetized with the aid of this anesthetic. Therefore, anesthetic must be refilled from time to time. According to the invention, the refill opening allows an anesthetic to be filled into the anesthetic tank, thereby topping up the anesthetic tank. This anesthetic comes, for example, from a container, in particular from a bottle, or from a supply line.

As a rule, the refilled anesthetic is liquid at room temperature. However, the boiling point of many anesthetics is in a temperature range that typically occurs in closed rooms, especially below 40° C., so that the anesthetic can easily evaporate. It is desirable that neither gaseous nor liquid anesthetic escapes into the environment of the anesthetic dispenser.

The closure for the refill opening can be moved from a closed position to an open position. In the closed position, the closure seals the refill opening, preferably fluid-tight, so that no anesthetic can escape from the anesthetic tank into the environment and also no fluid can flow into the anesthetic tank from the outside. The term "fluid-tight" includes the possibility that unavoidable gaps nevertheless exist between the closure and the anesthetic tank and that the refill opening is therefore not absolutely fluid-tightly closed.

If the anesthetic dispenser is in the operating mode, the closure is in the closed position. When the closure is in the open position, the anesthetic dispenser is in a refill mode. In the open position, the closure allows anesthetic to flow from a reservoir, such as a refill container or a stationary supply port, into the anesthetic tank, thereby refilling the anesthetic tank. In one embodiment, the closure comprises a tube that directs anesthetic into the anesthetic tank.

On its way from the closed position to the open position, the closure reaches an intermediate position. In this intermediate position, the closure also closes the refill opening and therefore prevents anesthetic from escaping from the anesthetic tank into the environment in any significant quantity. While the closure is moved from the closed position to the intermediate position, at least one transition period elapses.

According to the invention, the position sensor automatically detects the event that the closure has been moved out of the closed position. The position sensor is configured such that this event is already detected before the closure reaches the intermediate position, i.e. already during the transition period, preferably in the first quarter of the transition period. The position sensor eliminates the need for a human to provide a user input that the closure has now been moved. Rather, this event is automatically detected by the position sensor, and a message containing this information is automatically transmitted to the control unit. It is possible, but not necessary, that the event is detected that the closure has reached the intermediate position.

In response to the control unit receiving the message that the closure is being moved out of the closed position, the control unit automatically initiates the step of lowering the pressure in the anesthetic tank. In order to trigger a lowering of the pressure, the control unit controls the pressure reduction unit. This lowering is performed during the transition time period and causes the pressure to drop and become lower than the operating pressure. However, at least during the transition period, the pressure in the anesthetic tank remains above the ambient pressure, and the closure still closes the refill opening. In other words: during the transition period, there is positive pressure (overpressure) in the anesthetic tank relative to ambient. Because the closure closes the refill opening, no relevant amount of anesthetic can escape into the environment.

Preferably, a setpoint transition pressure is specified that is lower than the setpoint operating pressure and higher than the ambient pressure and can be constant over time or variable over time.

In one embodiment, the length of the transition time period is fixed. Preferably it is at least 5 sec, more preferably at least 10 sec, in particular at least 30 sec or 60 sec. In another embodiment, the transition time period ends when a specified event has occurred that depends on the actual pressure in the anesthetic tank. For example, the event has occurred when the actual pressure has dropped to the specified target transition pressure. A combination is also possible: the transition time period ends when a minimum time period has elapsed and the specified event has occurred, depending on which event occurred later.

In one embodiment, the control unit performs closed-loop control during the transition period. The regulating objective for this control is that the actual pressure in the anesthetic tank is equal to the setpoint transition pressure during the transition period.

According to the invention, at least the transition time period elapses between the detection that the closure has been moved out of the closed position and the opening of the refill opening. During this transition period, the refill opening is still closed. Therefore, during this transition time period, no anesthetic can escape from the anesthetic tank through the refill opening into the environment. The release of anesthetic into the environment is undesirable because people can be exposed to it. In addition, if anesthetic leaks into the environment, anesthetic is wasted.

The pressure in the anesthetic tank is lowered by the control unit in response to the detection that the closure has been moved out of the closed position and, after lowering, is lower than the operating pressure but still above the ambient pressure. Therefore, it is possible, but not required, that the refill container with anesthetic or the refill port be able to withstand the operating pressure. It is sufficient that they can withstand the lower pressure reached during the transition period. Even at this lower pressure, no anesthetic escapes from the anesthetic tank into the environment because the closure is still closed.

The pressure in the anesthetic tank remains above ambient pressure during the transition period. In many cases, the operating pressure as well as the reduced pressure above the ambient pressure, reduce the risk that anesthetic or carrier gas or other gas from the mixing unit enters the anesthetic line, whereby this anesthetic line leads from the anesthetic tank to the mixing unit, i.e. that anesthetic or carrier gas or other gas flows backwards. This is often undesirable because this anesthetic line is intended to conduct liquid anesthetic into the mixing unit and a gas mixture with a specified concentration of gaseous anesthetic is to be generated in the mixing unit. A backflow from the mixing unit into the anesthetic line can lead to gas bubbles in this anesthetic line. Gas bubbles in the anesthetic line can lead to the generation of a gas mixture in the mixing unit with an incorrect and/or strongly varying concentration of anesthetic over time and/or location, which is undesirable.

The invention can be used in combination with an anesthetic buffer tank. In one possible embodiment, this buffer storage holds liquid anesthetic and is arranged between the anesthetic tank and the mixing unit. In another possible embodiment, this buffer tank accommodates a gas mixture comprising at least one anesthetic and is arranged downstream of the mixing unit. The invention can also be combined with two buffer tanks, namely a buffer tank upstream and a buffer tank downstream from the mixing unit. However, the invention eliminates the need to provide such a buffer storage. Therefore, the invention saves space and results in a mechanically simpler configuration. If no buffer tank is provided, it also saves the need to monitor a buffer tank for leakage.

After the transition period has elapsed, the refill opening is preferably opened, for example, by means of an actuator that moves the closure away from the closed position. Or the refill opening can be opened manually, for example by unlocking a closure element so that it can be removed from the refill opening, and a user removes the closure from the refill opening.

In one embodiment of the invention, a desired or required value for the transition time period is specified. For example, the mechanical configuration of the closure dictates the transition time period: After the closure has been moved from the closed position, the refill opening remains closed during the transition time period, even if movement of the closure has already begun.

In one embodiment, the closure can be moved with the aid of an actuator unit, and a reduction gear is arranged between the actuator unit and the closure so that the transition period elapses. Thanks to the gear reduction, the actuator only needs to apply a relatively low force. Or the closure is difficult to move due to its configuration.

In one embodiment, the closure is moved relative to the refill opening from the closed position to the open position by two successive movements. In the first movement, the closure is rotated relative to the refill opening, for example along a thread, until the closure reaches the intermediate position. In the second movement, the closure is removed from the refill opening, preferably by a linear movement parallel to a longitudinal axis of the refill opening. Such a motion sequence is known from the process of opening the cap of a fuel tank for a vehicle with an internal combustion engine. The position sensor detects the start of the first, i.e. rotating, movement.

In another embodiment, the closure comprises the actual closure element and a flap. The closure element is located between the flap and the anesthetic tank. To open the refill opening, the flap is first opened, and then the closure element is removed from the refill opening. The flap protects the closure element from mechanical damage and contamination. In addition, the flap reduces the risk of the closing element being opened unintentionally.

These two embodiments can be combined with each other: The closure element is located between a flap and the anesthetic tank and can be moved by a rotating movement and by another movement out of the refill opening.

In a preferred embodiment, the position sensor is configured to detect the start of the process of moving the flap out of a closed position. In many cases, this configuration leads to a relatively long transition period: This transition period ends at the earliest when the flap is fully open and the actual closure element can now be removed or opened in another way. During this transition period, the closure element keeps the anesthetic tank closed even when the flap is open, so that no anesthetic can escape. It is also possible that the position sensor detects the process of the closure element being moved out of the closed position.

In another embodiment, a desired or required value for the refill pressure is specified, wherein this specified refill pressure value is above the ambient pressure but below the operating pressure. It is not necessary in this other embodiment to specify the length (duration) of the transition period. In one embodiment, this refill pressure value is above a maximum ventilation pressure—this is the maximum pressure that a ventilator applies while artificially ventilating and anesthetizing a patient using the generated gas mixture.

After the event that the closure has moved out of the closed position is detected, the control unit causes the pressure in the anesthetic tank to be lowered from the operating pressure to the specified refill pressure by means of a pressure control or a pressure regulation. The transition period ends when the pressure in the anesthetic tank has reached the specified refill pressure. The length of the transition time period thus depends on how quickly the pressure in the anesthetic tank is lowered to the refill pressure. This length does not need to be specified.

In one further embodiment of this other embodiment, the control unit is able to control a blocking unit for the closure of the refill opening. This blocking unit keeps the closure and thus the refill opening closed during the transition period, namely until the pressure in the anesthetic tank is reduced to the refill pressure.

On the one hand, the refill pressure can be set so low that the refill container with liquid anesthetic and the refill opening can withstand this refill pressure, in particular are not damaged, and no anesthetic escapes from the anesthetic tank into the environment. On the other hand, the refill pressure can be set high enough to minimize the risk of a gas mixture from the mixing unit flowing back into the anesthetic tank through the anesthetic line. Liquid anesthetic should normally flow through the anesthetic line. The backflow of such a gas mixture can lead to gas bubbles in the anesthetic line, which is undesirable as already explained above. A sufficiently high refill pressure reduces the risk of such gas bubbles occurring in the anesthetic line.

If the refill pressure is too low, these gas bubbles can be caused in particular by the ventilation pressure applied by the above-mentioned ventilator during artificial ventilation and anesthetization of the patient. Preferably, therefore, the specified refill pressure is at least as high as the maximum ventilation pressure, and particularly preferably even higher, especially at least 20% higher.

According to the invention, the anesthetic line conducts anesthetic from the anesthetic tank to the mixing unit. Generally, this anesthetic is liquid in the anesthetic line at a usual ambient temperature (room temperature) between 10° C. and 40° C. In a preferred embodiment, the control unit is able to control an anesthetic supply unit, in particular an injection valve. Depending on the control, the anesthetic supply unit optionally supplies anesthetic in the anesthetic line to the mixing unit or is switched off In one implementation, the switched-off anesthetic supply unit blocks the anesthetic line. When the anesthetic dispenser is operated in the operation mode, the anesthetic supply unit delivers anesthetic into the mixing unit.

According to the invention, the position sensor detects the event that the closure has been moved out of the closed position. Preferably, the control unit switches off the anesthetic delivery unit in response to the detection of this event. This configuration reduces the risk that the anesthetic delivery unit will still attempt to deliver anesthetic when the pressure is too low.

According to the invention, the position sensor detects the event that the closure has been moved out of the closed position. Detection of this event triggers the step of the controller lowering the pressure in the anesthetic tank. In one embodiment, the anesthetic dispenser includes a disposal line leading from the anesthetic tank to a gas intake or to the environment, preferably to a stationary disposal port. A controllable disposal shut-off means is able to selectively release or shut off the disposal line. The disposal line and the disposal shut-off means belong to the pressure reduction unit. When the anesthetic dispenser is operated in the operating mode, the disposal line is shut off After detecting the event that the closure has been moved out of the closed position, the control unit controls the disposal shut-off means, and the controlled disposal shut-off means releases the disposal line. Gaseous anesthetic can flow out of the anesthetic tank through the disposal line, lowering the pressure in the anesthetic tank. The disposal line leads preferentially to a receptacle or into the environment.

This configuration further reduces the risk of anesthetic escaping into the surroundings of the anesthetic dispenser. It is possible, but not necessary, to provide a buffer tank that takes in anesthetic when the pressure is reduced and releases it again later.

The invention further relates to a system configured and adapted to anesthetize a patient. This system comprises a ventilator configured to deliver a gas mixture comprising at least one anesthetic and oxygen to the patient, thereby anesthetizing the patient. Preferably, the ventilator performs a sequence of ventilatory breaths and delivers an amount of the gas mixture to the patient in each ventilatory breath of the sequence. The system further comprises an anesthetic dispenser according to the invention. The anesthetic dispenser is in fluid communication with the ventilator. A gas mixture comprising at least one anesthetic and a carrier gas comprising oxygen is passed through said fluid connection to the ventilator, said gas mixture having been generated in or by the mixing unit of the anesthetic dispenser.

Preferably, the ventilator generates a time-varying, in particular oscillating, ventilation pressure during artificial ventilation. Particularly preferably, the ventilator performs a sequence of ventilation strokes. Preferably, the pressure in the anesthetic tank remains above the maximum ventilation pressure that the ventilator builds up both when the anesthetic dispenser is operated in the operating mode and during the transition period. This reduces the risk of a gas mixture from the ventilator getting back to the feeder unit and further into the anesthetic line, creating gas bubbles.

In the following, the invention is described based on embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
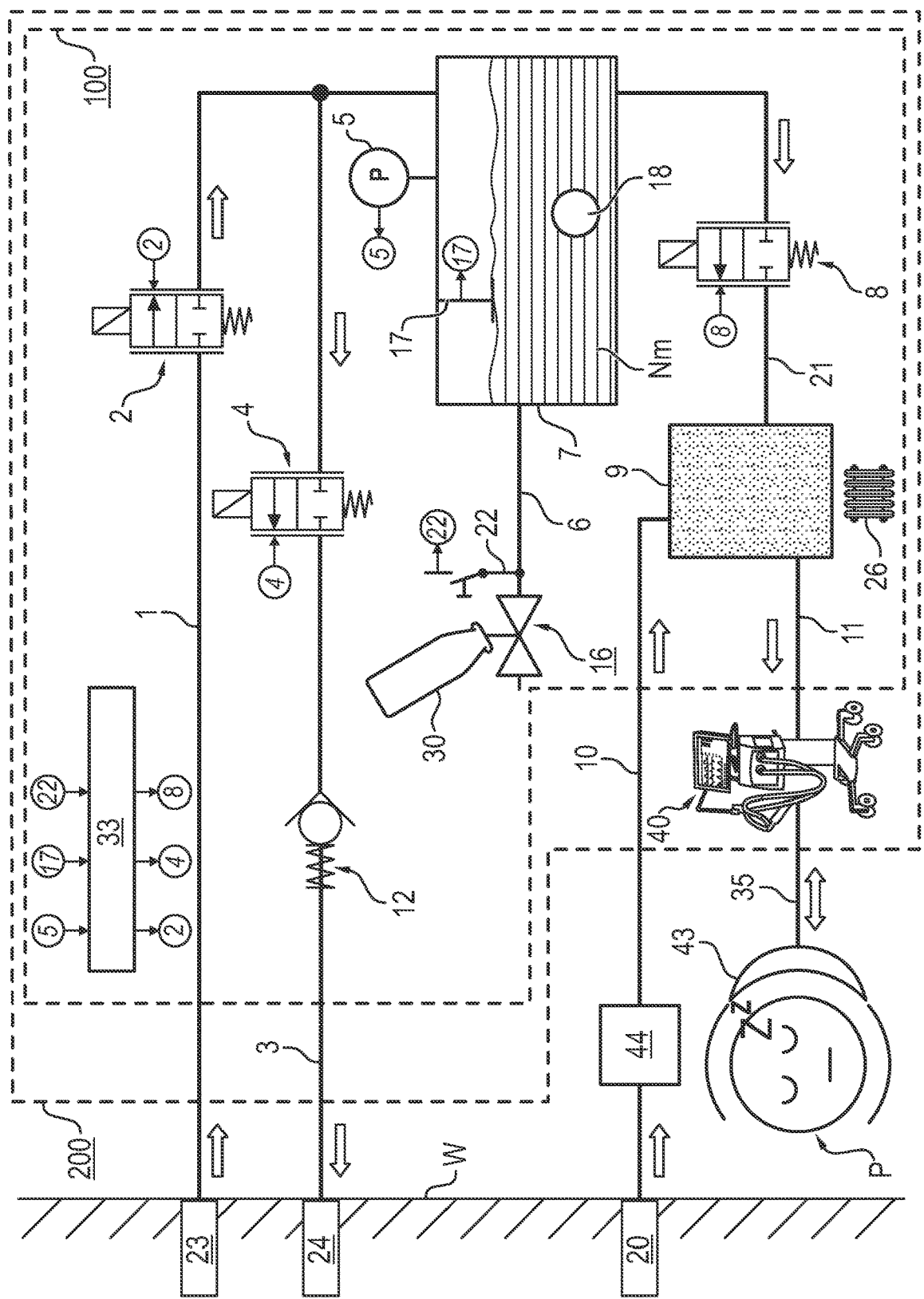
FIG. 1 is a schematic view of a first embodiment of the invention.

Referring to the drawings, in the embodiment examples, the invention is used for an anesthesia system. This anesthesia system supplies a completely or at least partially anesthetized patient P with a gas mixture comprising oxygen and/or breathing air and at least one gaseous anesthetic. The anesthesia system comprises a ventilator and at least one anesthetic dispenser according to the invention. Optionally, a second anesthetic dispenser according to the invention is available in reserve.

In the embodiments, the anesthetic is admixed with a carrier gas. The carrier gas comprises at least one, preferably two or all three, of the gases: breathing air; oxygen ($O_2$); and nitrous oxide ($N_2O$). The carrier gas is generated from the carrier gas components, and the anesthetic is fed (injected) into this carrier gas. The patient is supplied by the anesthesia system with a gas mixture comprising the carrier gas and the vaporized anesthetic.

FIG. 1 and FIG. 3 to FIG. 5 show several alternative embodiments of the anesthetic dispenser 100 according to the invention. In the following, the first embodiment is first described with reference to FIG. 1. The ventilator 40 is connected to a patient-side coupling unit 43 via a line arrangement 35. The patient-side coupling unit 43 is connected to the patient P and comprises, for example, a breathing mask on the face of the patient P or a tube or catheter in the body of the patient P. Preferably, the conduit arrangement 35 comprises a two-lumen tube so that a ventilation circuit is established between the patient P and the ventilator 40. This ensures that the gas exhaled by the patient P, which may contain anesthetic, is returned to the ventilator 40 and does not leak into the environment. A delivery unit of the ventilator 40 keeps the ventilation circuit going.

During artificial ventilation, the ventilator 40 performs a sequence of ventilation strokes. During each ventilation stroke, the ventilator 40 generates a pressure in the ventilation circuit that is above the ambient pressure and varies over time. The maximum pressure generated by the ventilator 40 during artificial ventilation is referred to herein as the "maximum ventilation pressure". Often, this maximum ventilation pressure is 20 hPa to 30 hPa above ambient pressure.

FIG. 1 further shows schematically the anesthesia system 200 configured to anesthetize the patient P and comprising the anesthetic dispenser 100.

A supply port 20 is installed in a wall W to provide the components of a carrier gas, preferably under positive pressure. The carrier gas components are fed to a carrier gas mixer 44, which generates the carrier gas from the supplied components. The carrier gas mixer 44 can be constructed as described in DE 10 2008 057 180 B3 (corresponding U.S. Pat. No. 8,356,596 B2 is incorporated herein by reference).

By means of a carrier gas line 10, the carrier gas is fed to a mixing tank 9 of the anesthetic dispenser 100. This mixing tank 9 belongs to the mixing unit of the embodiment. By means of an anesthetic line 21, the anesthetic Nm, which is liquid at room temperature, is supplied to this mixing tank 9. The mixing tank 9 and the anesthetic line 21 belong to the anesthetic dispenser 100, which generates gaseous anesthetic from the supplied liquid anesthetic Nm and mixes it with the carrier gas. In the embodiment shown, a heater 26 is in thermal contact with the mixing tank 9 and vaporizes or evaporates the supplied liquid anesthetic Nm. The gas mixture of the carrier gas and the gaseous anesthetic is supplied to the ventilator 40 by means of a gas mixture line 11.

In one embodiment, the anesthetic dispenser 100 includes a controllable injection (feed) valve 8 that can be turned on and off and functions as an anesthetic delivery unit. The switched-on injection valve 8 injects liquid anesthetic Nm into the mixing tank 9. The switched-off injection valve 8 does not inject any anesthetic and preferably shuts off the anesthetic line 21 so that no gas can flow to the anesthetic tank 7. Preferably, the volume flow at which the injection valve 8 injects liquid anesthetic can be varied to ensure a desired concentration of anesthetic Nm in the gas mixture formed in the mixing tank 9. It is also possible to additionally or instead change the volume flow of carrier gas through the carrier gas line 10. Both measures can help to bring the concentration of anesthetic in the gas mixture to a specified value with a tolerance.

The liquid anesthetic Nm is kept in stock in an anesthetic tank 7 and flows from this anesthetic tank 7 through the anesthetic line 21 to the mixing tank 9. In the anesthetic tank 7, the liquid anesthetic Nm is under positive pressure relative to the ambient pressure. More precisely, the gas in the anesthetic tank 7 above the liquid anesthetic Nm has an overpressure. Thanks to this overpressure, no pump is needed to deliver the liquid anesthetic Nm to the mixing tank 9. Rather, the positive pressure in conjunction with the injection valve 8 causes liquid anesthetic Nm to flow from the anesthetic tank 7 through the anesthetic line 21 into the mixing tank 9.

The overpressure in the anesthetic tank 7 should remain constant over time or follow a specified time curve. For example, the overpressure should be at least 1 bar, preferably 2 bar, above the ambient pressure. This overpressure is hereinafter referred to as "operating pressure". The following is an exemplary description of how the overpressure is regulated or controlled.

A discharge line 3 connects the anesthetic tank 7 to a disposal connection 24 in the wall W. This disposal connection 24 is in fluid communication with a stationary fluid network. A controllable valve 4 is arranged in the discharge line 3. When valve 4 is open, gaseous anesthetic can flow through discharge line 3 to disposal port 24. This reduces the pressure in the anesthetic tank 7 and prevents this anesthetic from escaping into the environment. A check valve 12 prevents gas from flowing from the disposal connection 24 through the discharge line 3 to the anesthetic tank 7.

A pressure sensor 5 measures a measure of the current pressure in the anesthetic tank 7. Preferably, the pressure sensor 5 measures the positive pressure of the gas in the anesthetic tank 7 relative to the ambient pressure. The pressure in the anesthetic tank 7 is built up and can be increased by supplying compressed air or other pressurized gas from a port 23 in the wall W through the pressure line 1 into the anesthetic tank 7. A controllable valve 2 in the pressure line 1 is capable of optionally completely opening or completely closing the pressure line 1 in two end positions. Optionally, the valve 2 is configured as a proportional valve or as a switching valve. To increase the pressure in the anesthetic tank 7, the valve 2 is opened. When the valve 2 is closed, the pressure in anesthetic tank 7 decreases by itself when liquid anesthetic Nm flows out of anesthetic tank 7 through anesthetic line 21.

In addition, the pressure in the anesthetic tank 7 can be reduced in a controllable manner by opening valve 4 and allowing gas to flow through discharge line 3 to disposal connection 24. In this flow direction, the check valve 12 opens if the pressure in the anesthetic tank 7 is above a pressure barrier which opens this check valve 12. In one embodiment, the pressure barrier at which the check valve 12 opens can be changed by an external control. In another embodiment, this pressure barrier is fixed by the design of the check valve 12, in particular by the ratio between the opening area and the spring force of the check valve 12, so that control from the outside is not necessary.

Preferably, in the operating mode, the pressure in the anesthetic tank 7 is controlled so that a constant operating pressure is maintained. This operating pressure makes it possible to produce (generate) a desired concentration of the anesthetic Nm in the gas mixture in the mixing tank 9. In one embodiment, the actual pressure in the anesthetic tank 7 is controlled with the control objective that the actual pressure is constantly equal to a specified target operating pressure.

The liquid anesthetic Nm in the anesthetic tank 7 is gradually consumed. A measure of the amount of liquid anesthetic Nm currently present in the anesthetic tank 7 is measured. In the embodiment example, a level sensor 17 comprises a float and measures the current level of liquid anesthetic Nm in the anesthetic tank 7. Alternatively, or in addition to the level sensor 17, a viewing window 18 is provided in a wall of the anesthetic tank 7. A person or also a camera can perceive the current fill level through the viewing window 18.

A signal-processing control unit (controller) 33 receives readings from sensors 5, 17, and 22 and automatically controls valves 2, 4, 8, 19.

Because the anesthetic Nm is consumed, it is necessary to refill liquid anesthetic Nm from time to time. A tubular round or n-corner refill opening 6 is arranged on the anesthetic tank 7 (n>=3), which is configured to direct liquid anesthetic into the anesthetic tank 7. In the embodiment, a bottle 30 with liquid anesthetic can be placed onto this refill opening 6 from above, and the liquid anesthetic flows from the bottle 30 diagonally downward through the refill opening 6 into the anesthetic tank 7. The bottle 30 can be placed onto the refill opening 6 in such a way that only a small amount of anesthetic escapes, ideally no anesthetic at all.

A closure 16 can be moved back and forth between a closed position and an open position. In the open position, the closure 16 allows liquid anesthetic Nm to flow from the bottle 30 through the refill opening 6 and into the anesthetic tank 7. In the closed position, the closure 16 closes the refill opening 6 fluid-tightly and prevents liquid or gaseous anesthetic from escaping from the anesthetic tank 7 into the environment.

Figure 2:
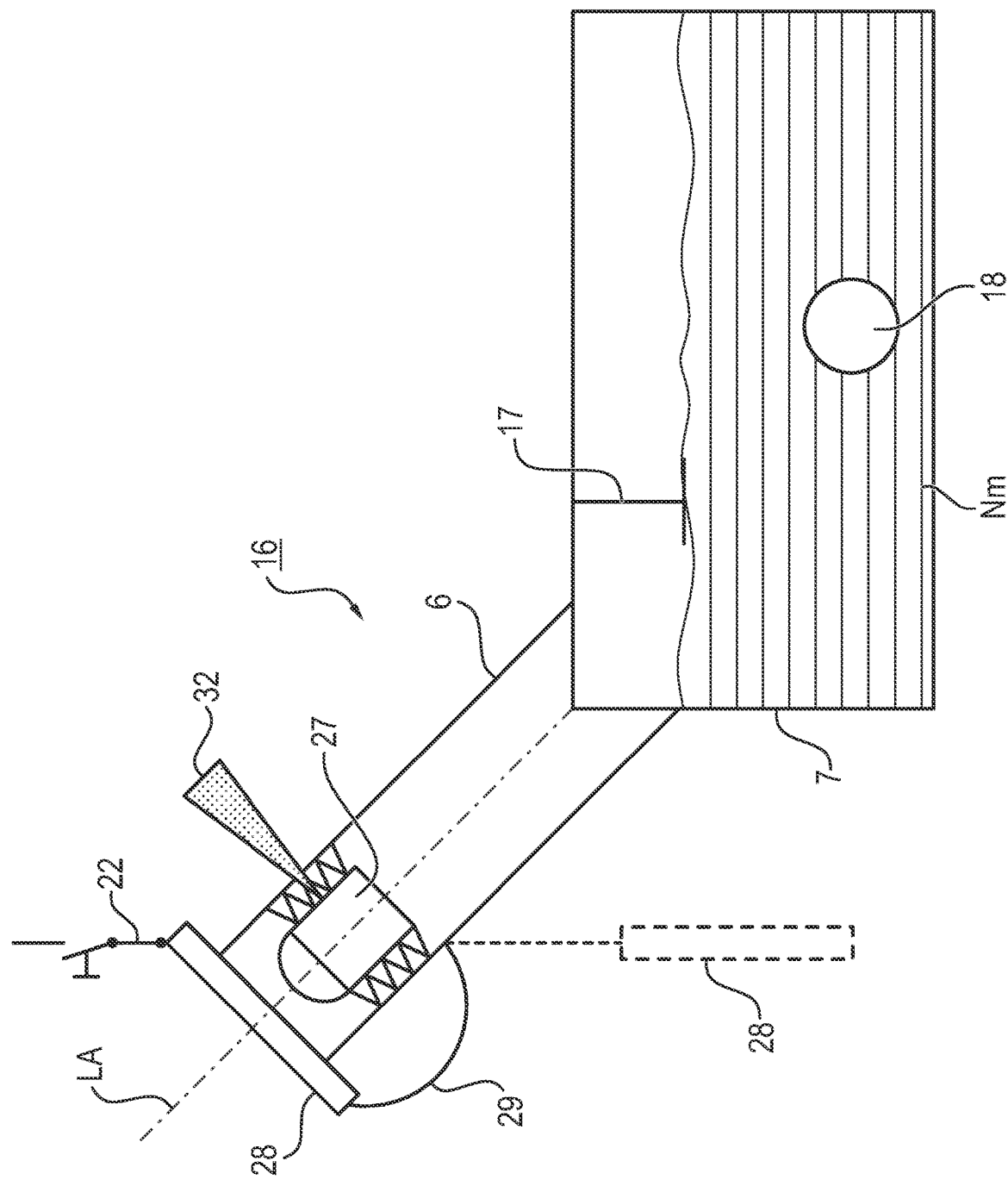
FIG. 2 is a schematic view an embodiment of the closure.

FIG. 2 shows a detailed view of a preferred embodiment of the refill opening 6 and the closure 16. The tubular, round or n-corner refill opening 6 extends along a longitudinal axis LA. According to this embodiment, the closure 16 comprises a closure element 27 that is capable of selectively closing or opening the refill opening 6. For example, the closure element 27 is held in the refill opening 6 in a fluid-tight manner by means of two corresponding threads arranged on the outer wall of the closure element 27 and on the inner wall of the refill opening 6, respectively. To release the refill opening 6, the closure element 27 is removed from the refill opening 6 by two successive movements. In the first movement, the closure element 27 is rotated about the longitudinal axis LA of the refill opening 6, for example in a thread of the refill opening 6. After the first movement, the closure element 27 has reached an intermediate position in which it still closes the refill opening 6. In the second movement, the closure element 27 is removed from the refill opening 6, preferably by a linear movement parallel to the longitudinal axis LA, so that the refill opening 6 is open. Such a sequence of two movements is known from the operation of opening a fuel tank for a vehicle with an internal combustion engine.

In one embodiment, the closure 16 additionally comprises a flap 28. The closure element 27 is located between the flap 28 and the anesthetic tank 7. Both when the flap 28 is closed and when it is open, the closure element 27 closes the refill opening 6. To open the closure 16, the flap 28 is first opened, and then the closure element 27 is removed from the refill opening 6. In the embodiment with the flap 28, the closure element 27 is also removed from the refill opening 6 by the two successive movements just described, or by a single movement. A condition in which the flap 28 is open and the closure element 27 is still in the refill opening 6 may be referred to as an intermediate position of the closure 16. Preferably, a chain (tether) 29 holds the flap 28 to the refill opening 6 to prevent the flap 28 from being lost.

A position sensor 22, shown schematically, detects the event that the flap 28 has moved out of the closed position. In the embodiment with the flap 28, more time is available after the detection of the event that the flap 28 has been moved until the refill opening 6 is opened.

In an embodiment without a flap 28, the position sensor 22 detects the event that the closure element 27 has been moved out of the closed position. Also, in the embodiment with the flap 28, the position sensor 22 may detect movement of the closure element 27.

Also shown in FIG. 2 is a blocking unit 32 which is capable of selectively blocking or releasing the closure element 27. The closure element 27, blocked by the blocking unit 32, is held in the refill opening 6 and can preferably be moved back and forth between the closed position and the intermediate position, but cannot be removed from the refill opening 6. Therefore, the blocked closure element 27 closes the refill opening 6. The closure element 27 can be removed from the refill opening 6 when the blocking unit 32 has released the closure element 27.

In one embodiment, a presence sensor (not shown) determines whether or not a closure element 27 is actually present in the refill opening 6 when the flap 28 is closed. The absence of a closure element 27 when the flap 28 is closed is an error. If it is detected that there is no closure element 27 in the refill opening 6 when the flap 28 is closed, an alarm is preferably generated in a form that can be perceived by a human being. This is because if flap 28 were opened when closure element 27 was missing, the pressure in anesthetic tank 7 would drop abruptly to ambient pressure and anesthetic would escape, which is undesirable.

The refill opening 6 can, for example, be configured as described in WO 2020/030408 A1 (corresponding US 2021290887 A1 is incorporated herein by reference).

The invention makes it possible for liquid anesthetic Nm to be replenished even while the patient P is connected to the ventilator 40 via the patient-side coupling unit 43 and is anesthetized. Thanks to the invention, the supply of the gas mixture of the anesthetic and the carrier gas to the patient P is interrupted only briefly enough to allow the ventilator 40 to maintain the supply of anesthetic to the patient P during this brief interruption without any gas mixture flowing through the gas mixture conduit 11 to the ventilator 40. For example, the ventilator 40 comprises its own buffer tank, and/or the gas mixture line 11 acts as a buffer tank. Preventing the patient P from waking from anesthesia during the refill. The invention also reduces the risk of any of the following adverse events occurring during refilling of liquid anesthetic Nm:

Gaseous anesthetic escaping from the anesthetic tank 7 through the open refill opening 6 into the environment.

Because the injection valve 8 is open or spaced from the mixing tank 9 and the pressure in the anesthetic tank 7 is low, gaseous anesthetic flowing from the mixing tank 9 into the anesthetic line 21, where it forms gas bubbles in the liquid anesthetic Nm.

Due to insufficient pressure in the anesthetic tank 7, the carrier gas in the mixing tank 9 no longer being enriched with sufficient gaseous anesthetic.

Due to insufficient pressure, the anesthetic Nm starting to boil.

In the embodiment example, the pressure in the anesthetic tank 7 is gradually lowered when anesthetic Nm is refilled into the anesthetic tank 7. This is described below.

The refill opening 6 cannot be opened abruptly, but only gradually and/or with a time delay. This time delay results from the fact that the closing element 27 must first be moved to the intermediate position and/or the flap 28 must first be opened. The position sensor 22 at the refill opening 6 detects the event that the process has started to open the refill opening 6. For example, the position sensor 22 detects the event that the first movement of the closure element 27 has been started, i.e. the closure element 27 is rotated out of the closed position. Or, the position sensor 22 detects the event that the closure 28 is moved out of the closed position. The position sensor 22 may comprise a contact sensor, in particular a sensor that detects whether an electrical connection is closed or open. The position sensor 22 may also include, for example, a photoelectric sensor, an RFID sensor, and/or a Hall sensor.

Various such sensors are described in EP 2 170 447 B1 (U.S. patent application Ser. No. 10,406,313 (B2) is incorporated herein by reference). Detection of this event triggers the first step described below.

In the first step, the pressure in the anesthetic tank 7 is reduced from the operating pressure to a specified pressure. This pressure, which is produced during the refilling of anesthetic Nm, is referred to below as the "refill pressure". The refill pressure is less than the above-mentioned operating pressure maintained when the refill opening 6 is closed and sufficient anesthetic Nm is in the anesthetic tank 7, but preferably greater than the ambient pressure. The specified refill pressure may depend on the anesthetic used.

Preferably, the refill pressure is above the maximum ventilation pressure generated by the ventilator 40 when artificially ventilating patient P. This reduces the risk of the ventilation pressure forcing a gas mixture back into the mixing tank 9 or even into the anesthetic line 21, which can lead to undesirable gas bubbles. In one embodiment, this refill pressure is preferably 50 hPa to 100 hPa above ambient pressure. This refill pressure is generally sufficient to safely prevent gaseous anesthetic from entering the anesthetic line 21 from the mixing tank 9. On the other hand, the bottle 30 on the refill opening 6 can withstand this pressure.

If the anesthetic Nm can boil at room temperature and becomes liquid, the refill pressure is higher. For example, desflurane has a boiling point of 23° C., which is why a refill pressure of 500 to 1000 hPa above ambient pressure is used. The bottle 30 containing such an anesthetic is able to withstand this refill pressure. At this refilling pressure, it is possible to keep the injection valve 8 open so that anesthetic Nm is also injected into the mixing tank 9 during refilling. This design is particularly important because the anesthetic effect of desflurane decreases rapidly when the supply of a gas mixture containing desflurane to patient P is reduced.

During this first step, the refill opening 6 preferably remains completely closed. For example, a radially acting seal completely seals the refill opening 6 during the first step. Even when the refill opening 6 is partially open, the free diameter of the refill opening 6 at the end of the first step is still so small that only a small amount of anesthetic can escape from the anesthetic tank 7 into the environment. During the first step, the closure 16 is moved from the closed position to the intermediate position. For example, the flap 28 is opened.

In one embodiment, the control unit 33 is able to control the closure 16 or the blocking unit 32 for the closure 16. The control causes the closure 16 to keep the refill opening 6 closed until the pressure in the anesthetic tank 7 is reduced to the refill pressure and thus the first step is completed. Only then does the control unit 33 release the closure 16, thus allowing the closure 16 to move from the intermediate position to the open position. In another embodiment, the mechanical design of the refill opening 6 ensures that the refill opening 6 remains closed for a sufficiently long time without the need for external actuation, in particular without the need for actuation of a blocking unit. For example, the closure 16 is sufficiently sluggish so that a sufficiently long period of time elapses until the closure 16 has reached the intermediate position.

The first step is terminated when the pressure in the anesthetic tank 7 has been lowered or has dropped to the specified refill pressure. The termination of the first step can be triggered by the expiration of a time period or by an event, namely that the pressure in the anesthetic tank 7 has been lowered to the refill pressure.

In the second step, the refill opening state of opening 6 is adjusted until it is completely open. For example, the closure element 27 is removed from the refill opening 6. The bottle 30 is placed gas-tightly on the refill opening 6, and liquid anesthetic Nm flows from the bottle 30 into the anesthetic tank 7.

Two different embodiments of the second step are possible. In a first embodiment, the bottle 30 and the connection between the bottle 30 and the refill opening 6 are pressure resistant such that this connection can withstand the refill pressure in the anesthetic tank 7 that was produced in the first step. In this embodiment, preferably the injection valve 8 remains on during the second step. It is also possible that the injection valve 8 is switched off beforehand. Even while liquid anesthetic Nm flows from the bottle 30 into the anesthetic tank 7, anesthetic Nm passes from the anesthetic tank 7 through the anesthetic line 21 into the mixing tank 9 due to the excess pressure in the anesthetic tank 7.

In another embodiment, it is also possible, but not required, that the bottle 30 and the connection be able to withstand the refill pressure. In this alternate embodiment, preferably the bottle 30 is in fluid communication with the environment. Rather, in this other embodiment, the injection valve 8 is turned off in the second step. When the refill opening 6 is open, the pressure in the anesthetic tank 7 drops, i.e., drops below the refill pressure and, in extreme cases, down to ambient pressure. In one embodiment, an overpressure is still present in the mixing tank 9. The refill pressure and optionally the closed injection valve 8 prevent anesthetic or a gas mixture from flowing from the mixing tank 9 back into the anesthetic tank 7. The gas mixture present in a buffer tank of the ventilator 40, which is not shown, is sufficient to still supply the patient P with anesthetic for a certain period of time.

As soon as the bottle 30 is empty or the anesthetic tank 7 is filled, the bottle 30 is removed from the refill opening 6 again, the refill opening 6 is closed, and the pressure in the anesthetic tank 7 is increased again, at least to the refill pressure, preferably to a higher pressure than the refill pressure, particularly preferably back to the operating pressure.

Figure 3:
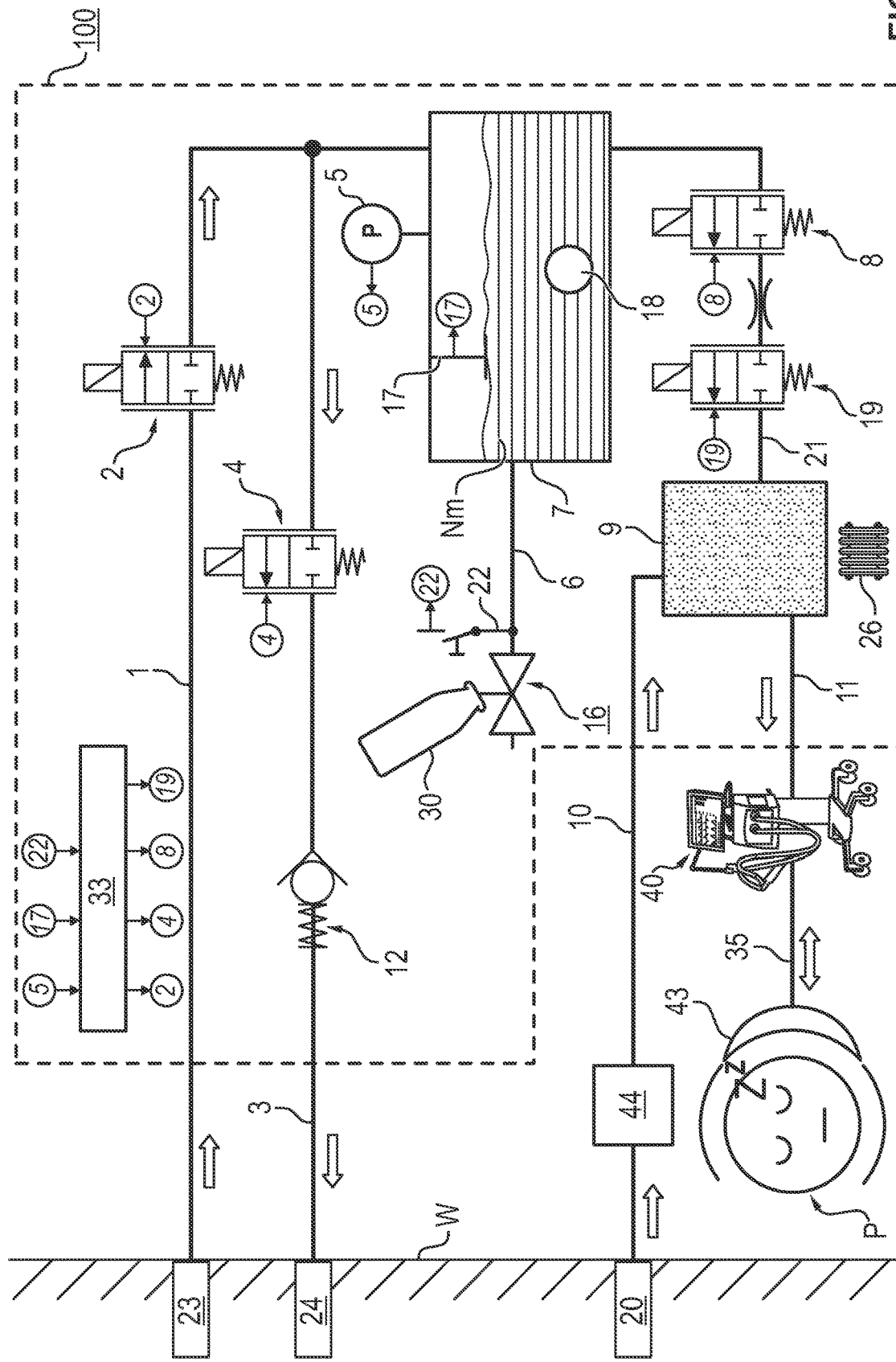
FIG. 3 is a schematic view of a variation of the first embodiment according to FIG. 1.

FIG. 3 shows a variation of the first design according to FIG. 1. The same reference signs have the same meaning as in FIG. 1. The valve 8 in the anesthetic line 21 is configured as a throttle valve. A second valve 19 can also shut off the anesthetic line 21 independently of the throttle valve 8. This configuration creates redundancy, particularly in the event that a valve 8 or 19 does not close the anesthetic line 21 due to a fault.

In another variation not shown, the check valve 12 is omitted. The valve 4 is a proportional valve that can be controlled from outside. In order to lower the pressure in the anesthetic tank 7, the valve 4 is first fully opened by the control. When the measured pressure in the anesthetic tank 7 approaches a specified pressure from above, the valve 4 is partially closed. This configuration makes it easier to bring the pressure in the anesthetic tank 7 to the desired refill pressure in the first step by controlling it.

Figure 4:
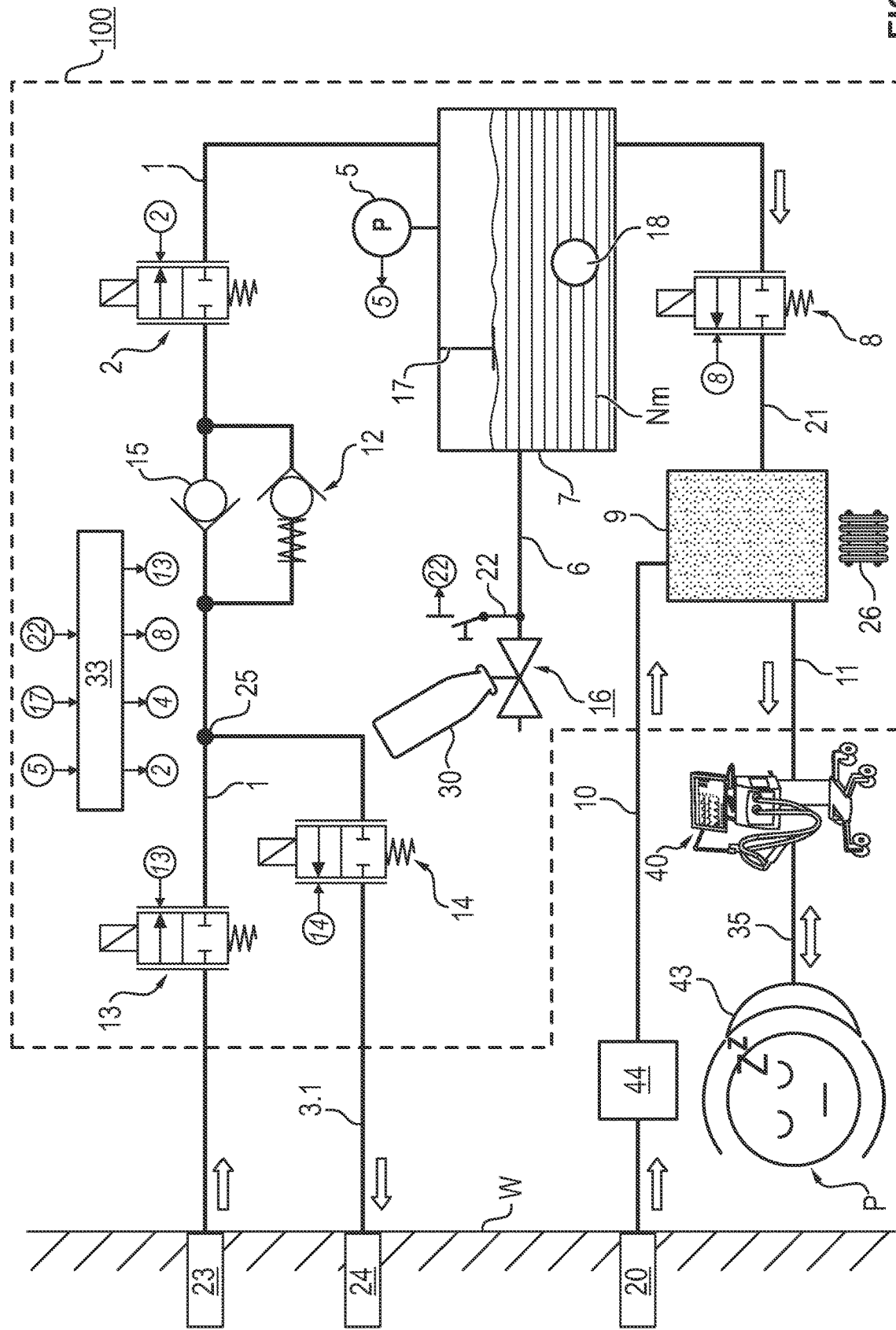
FIG. 4 is a schematic view of a second embodiment of the invention.

FIG. 4 shows a modification in which the discharge line 3 is replaced by a discharge line 3.1. The same reference signs have the same meaning as in FIG. 1. The discharge line 3.1 to the disposal connection 24 branches off from the pressure line 1 at a branching point 25, whereby the pressure line 1 in turn conducts compressed air from the supply connection 23 to the anesthetic tank 7.

To increase the pressure in the anesthetic tank 7, valve 13 is opened and valve 14 is closed. Check valve 15 in line 1 allows compressed air to pass from supply port 23 to valve 2 and on to anesthetic tank 7. To lower the pressure in the anesthetic tank 7, valve 13 is closed and valve 14 is opened. The spring-loaded check valve 12 maintains a residual pressure, for example the refill pressure, in the anesthetic tank 7. The check valve 15 closes the pressure line 1.

Figure 5:
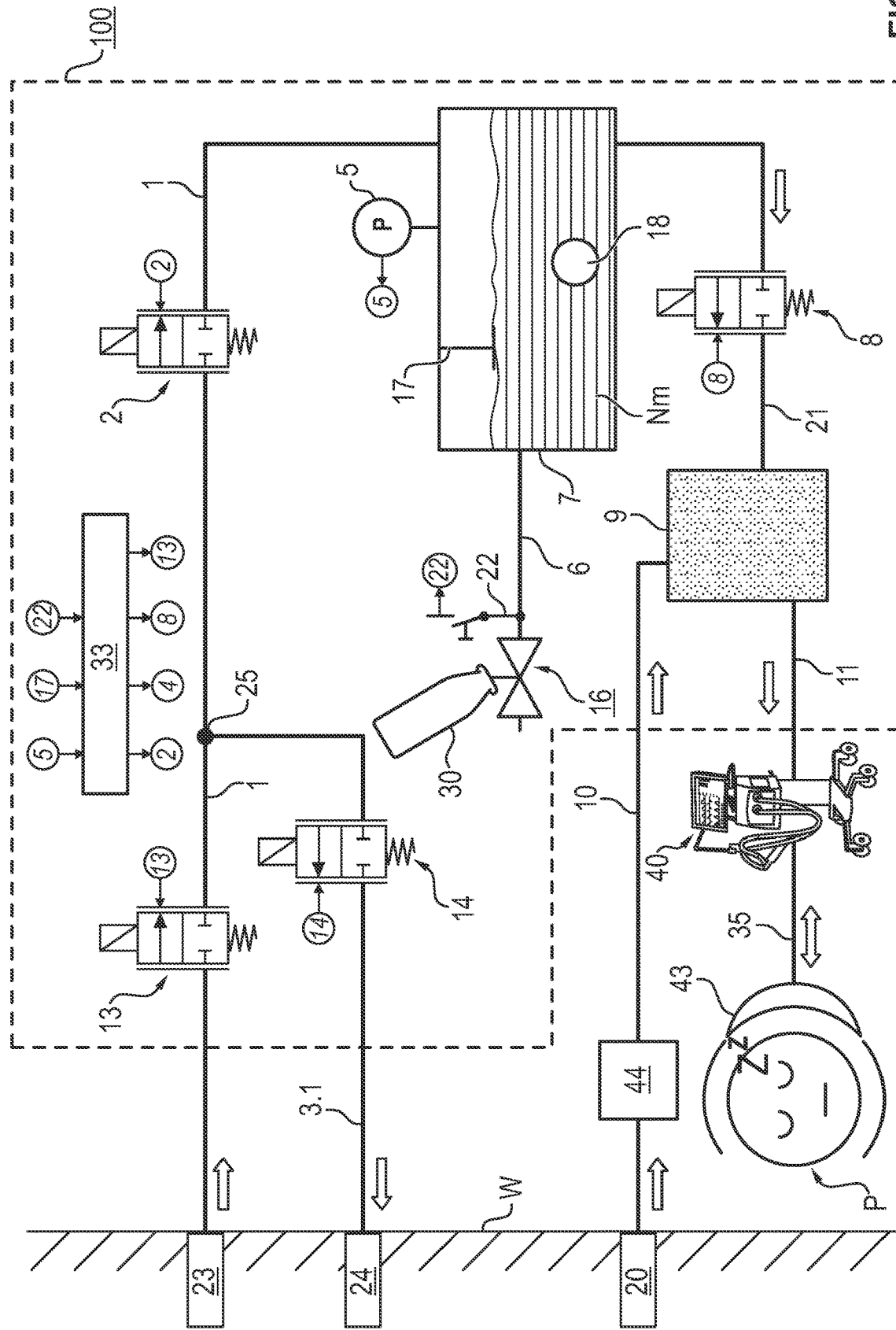
FIG. 5 is a schematic view of a third embodiment of the invention.

FIG. 5 shows a further possible configuration. The same reference signs have the same meaning as in FIG. 1. Just as in the embodiment according to FIG. 4, the discharge line 3.1 branches off from the pressure line 1 at the branching point 25. To allow compressed air to flow into the anesthetic tank 7, valve 13 is opened and valve 14 is closed. To reduce the pressure in the anesthetic tank 7, valve 13 is closed and valve 14 is opened. When valve 2 is open, gas can flow through pressure line 1, while when valve 2 is closed, line 1 is closed. Optionally, the valve 2 is configured as a controllable proportional valve.

Figure 6:
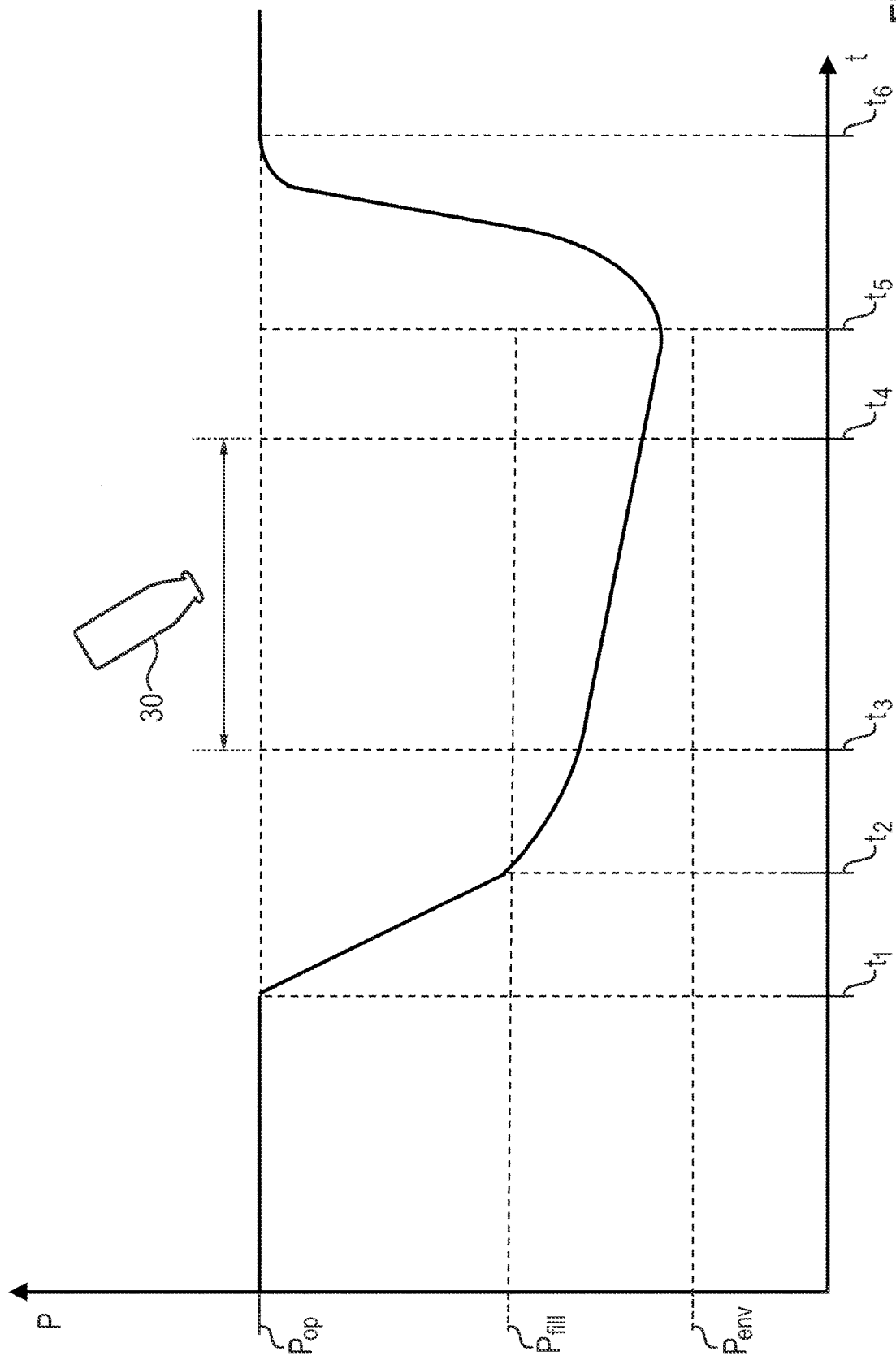
FIG. 6 is a graph showing an exemplary time course of the pressure in the anesthetic tank during refilling.

FIG. 6 shows an exemplary time course of the pressure in the anesthetic tank 7 during refilling. The time t is represented on the x-axis, and the pressure P in the anesthetic tank 7 is represented on the y-axis, namely as overpressure relative to a reference pressure.

Until the time ti, the control unit 33 maintains a constant operating pressure $P_{op}$, for example by means of regulation. The refill opening 6 and valve 4 (FIG. 1, FIG. 3) and valve 14 (FIG. 4, FIG. 5) are closed, the injection valve 8 delivers liquid anesthetic Nm, and valve 2 and valve 19 (FIG. 3), valve 13 (FIG. 4, FIG. 5) are temporarily opened to increase the pressure P.

At time $t_1$, the contact sensor (position sensor) 22 detects the event that the closure 16 has moved out of the closing position. In response to this detection, the control unit 33 causes the pressure in the anesthetic tank 7 to drop to a refill pressure $P_{fill}$ that is above the ambient pressure $P_{env}$. For this purpose, valve 2 and valve 13 (FIG. 4, FIG. 5) are closed and valve 4 (FIG. 1, FIG. 3) and valve 14 (FIG. 4, FIG. 5) are opened. The injection valve 8 is switched off. The closure 16 is moved from the closed position to the intermediate position and the refill opening 6 remains closed.

At time $t_2$, the pressure sensor 5 detects that the pressure P in the anesthetic tank 7 has dropped to the refill pressure $P_{fill}$. The time period from $t_1$ to $t_2$ is the transition time period within the meaning of the patent claims. In response to this detection, the control unit 33 causes the closure 16 to move to the open position or at least to be released and thus the refill opening 6 is opened or at least can be opened. At time $t_3$, the closure 16 is in the open position, and the refill opening 6 is open. The bottle 30 is placed on the refill opening 6 and enters the refill opening 6. Liquid anesthetic Nm flows from the bottle 30 into the anesthetic tank 7. The pressure in the anesthetic tank 7 continues to drop because the refill opening 6 is open. In the embodiment example, however, the pressure P remains above the ambient pressure $P_{env}$.

If sufficient anesthetic Nm has flowed from the bottle 30 into the anesthetic tank 7, the bottle 30 is removed from the refill opening 6. For example, the level sensor 17 detects that the anesthetic tank 17 now contains sufficient liquid anesthetic Nm, and a corresponding message is output. Or a user detects that the bottle 30 is empty or the anesthetic tank 7 is full.

At time $t_4$, the bottle 30 is removed from the refill opening 6 again. The closure 16 is closed again. At time $t_5$, the contact sensor 22 detects that the closure 16 is in the closed position again. In the time interval between $t_3$ and $t_4$, the anesthesia system 200 is in refill mode.

In one embodiment, the control unit 33 automatically triggers the step at time $t_5$ for the pressure P in the anesthetic tank 7 to rise again to the operating pressure $P_{op}$. Alternatively, a corresponding message is displayed to a user, the user is asked to confirm or reject, and the control unit 33 causes the pressure to rise after a corresponding confirming user input is detected. In order to increase the pressure in the anesthetic tank 7, valve 2 and valve 19 (FIG. 3) or valve 13 (FIG. 4, FIG. 5) are opened to increase the pressure P until the operating pressure $P_{op}$ is reached. Valve 4 (FIG. 1, FIG. 3) and valve 14 (FIG. 4, FIG. 5) are closed. In addition, the injection valve 8 is switched on again.

At time $t_6$, the pressure sensor 5 detects that the operating pressure $P_{op}$ has been reached again. At this point at the latest, the injection valve 8 is switched on again. The anesthesia system 200 is in operating mode again.

In summary, the invention relates to an anesthetic dispenser having a mixing unit and an anesthetic tank, and a process for generating (forming) a gas mixture using such an anesthetic dispenser. In the mixing unit, an anesthetic from the anesthetic tank is mixed with a carrier gas, thereby generating a gas mixture. Liquid anesthetic can be refilled into the anesthetic tank through a refill opening. In one operating mode of the anesthetic dispenser, the pressure is at a specified operating pressure. A closure can be moved from a closed position, via an intermediate position, to an open position, and closes the refill opening in both the feed position and the intermediate position. When the closure is moved from the closed position to the intermediate position, a transition period elapses. A position sensor detects the event that the closure has been moved out of the closed position. In response to this detection, the pressure in the anesthetic tank is lowered during the transition period to a refill pressure that is still above ambient pressure. The closure is then opened.

While specific embodiments of the invention have been shown and described in detail to illustrate the application of the principles of the invention, it will be understood that the invention may be embodied otherwise without departing from such principles.

| List of reference designations | |
| --- | --- |
| 1 | Line from supply port 23 to anesthetic tank 7 |
| 2 | Valve in discharge line 1 |
| 3 | Discharge line from anesthetic tank 7 to disposal connection 24 |
| 3.1 | Discharge line from branching point 25 to disposal connection 24 |
| 4 | Valve in the line 3 |
| 5 | Pressure sensor for measuring the pressure in the anesthetic tank 7 |
| 6 | Refill opening in the anesthetic tank 7, extends along the longitudinal axis LA, is selectively released or closed by the closure 16 |
| 7 | Anesthetic tank for liquid anesthetic Nm, comprises pressure sensor 5, level sensor 17 and viewing window 18, connected to mixing tank 9 via anesthetic line 21 |
| 8 | Valve for closing the anesthetic line 21 |
| 9 | Mixing tank, generates a gas mixture of the carrier gas and the anesthetic Nm, connected to the gas mixer 14 and the ventilator 40, is heated by the heater 26, is connected to the anesthetic tank 7 via the anesthetic line 21, to the carrier gas mixer 44 via the carrier gas line 10, and to the ventilator 40 via the gas mixture line 11 |
| 10 | Carrier gas line through which carrier gas flows from carrier gas mixer 44 to mixing tank 9 |
| 11 | Gas mixture line from mixing tank 9 to ventilator 40 |
| 12 | Check valve in the line 3 |
| 13 | Valve in discharge line 1 |

-continued

List of reference designations

| | |
|---|---|
| 14 | Valve in the pressure line 3.1 |
| 15 | Check valve in the pressure line 1 |
| 16 | Closure for refill opening 6, releases refill opening 6 after the transition time period [t1, t2] has elapsed |
| 17 | Level sensor for the anesthetic tank 7 |
| 18 | Viewing window in the anesthetic tank 7 |
| 19 | optional second valve in the anesthetic line 21 |
| 20 | Supply connection in the wall W for carrier gas |
| 21 | Anesthetic line, conducts liquid anesthetic Nm from anesthetic tank 7 to mixing tank 9 |
| 22 | Position sensor at the refill opening 6, detects the event that the closure 16 was moved out of the closed position |
| 23 | Supply connection for compressed air in the wall W |
| 24 | Disposal connection in the wall W to take in gas mixture |
| 25 | Branching point at which line 3.1 branches off from pressure line 1 |
| 26 | Heater for the mixing tank 9 |
| 27 | Closure element in the refill opening 6, in one embodiment is held in the refill opening 6 by the blocking unit 32 |
| 28 | Flap capable of opening or closing the refill opening 6 |
| 29 | Chain holding the flap 28 at the refill opening 6 |
| 30 | Bottle with liquid anesthetic, can be placed on the refill opening 6 |
| 32 | Blocking unit which prevents the closure 16 from being opened in the transition time period $t_1$, $t_2$ |
| 33 | data processing control unit, receives measured values from sensors 5, 17, 19, 22, controls valves 2, 4, 8, 13, 14 and the blocking unit 32 |
| 35 | Line arrangement between the ventilator 40 and the patient-side coupling unit 43 |
| 40 | Ventilator, connected by means of the gas mixture line 11 to the mixing tank 9 and by means of the line arrangement 35 to the patient-side coupling unit 43, performs ventilation strokes |
| 43 | patient-side coupling unit, connected to the ventilator 40 by the line arrangement 35 |
| 44 | Carrier gas mixer, which generates the carrier gas and is connected to the supply port 20, is connected to the mixing tank 9 via the carrier gas line 10 |
| 100 | anesthetic dispenser according to the invention, comprises the mixing tank 9, the injection valve 8, the heater 26, the anesthetic tank 7 and the control unit 33 |
| 200 | System for anesthetizing patient P, includes anesthetic dispenser 100, ventilator 40, and carrier gas mixer 44 |
| LA | Longitudinal axis and also central axis of the refill opening 6 |
| Nm | liquid anesthetic, can be filled into the anesthetic tank 7 |
| P | Patient connected to the patient-side coupling unit 43 and supplied with a mixture of carrier gas and anesthetic via the line arrangement 35 and thereby anesthetized by the system 200 |
| $P_{env}$ | Air pressure in the vicinity of the anesthetic dispenser 100 |
| $P_{fill}$ | Refill pressure in the anesthetic tank 7, is lower than the operating pressure Pop and is preferably above the maximum ventilation pressure generated by the ventilator 40 |
| $P_{op}$ | Operating pressure in anesthetic tank 7 |
| $t_1$ | Time at which the position sensor 22 detects the event that the closure 16 has been moved out of the closed position |
| $t_2$ | Time at which the pressure sensor 5 detects that the pressure in the anesthetic tank 7 has dropped to the refill pressure Pfill |
| $t_3$ | Time at which the bottle 30 is placed on the refill opening 6 |
| $t_4$ | Time that the bottle 30 is taken from the refill opening 6 |
| $t_5$ | Time at which the position sensor 22 detects the event that the closure 16 has reached the closed position again |
| $t_6$ | Time at which the pressure sensor 5 detects that the operating pressure $P_{op}$ has been reached in the anesthetic tank 7. |
| W | Wall with the supply connection 20, the supply connection 23 and the disposal connection 24 |

What is claimed is:

1. An anesthetic dispenser comprising:

a mixing unit configured to generate a gas mixture comprising at least one anesthetic and a carrier gas;

an anesthetic tank with a refill opening;

a closure for the refill opening, the closure being configured to move from a closed position via an intermediate position to an open position and being configured to close the refill opening in the closed position and in the intermediate position and release the refill opening in the open position;

an anesthetic line leading from the anesthetic tank to the mixing unit;

a controllable pressure increasing unit configured to increase pressure in the anesthetic tank or to effect such a pressure increase;

a controllable pressure reduction unit configured to reduce pressure in the anesthetic tank or to effect such a pressure reduction;

a pressure sensor configured to measure a value indicative of the pressure in the anesthetic tank;

a position sensor configured to detect an event that the closure has been moved out of the closed position, wherein the anesthetic dispenser is configured such that a transition time period elapses when the closure is moved from the closed position to the intermediate position; and a signal processing control unit configured:
to receive measured values from the pressure sensor and the position sensor;
to trigger an increase in pressure in the anesthetic tank by controlling the pressure increasing unit;
to trigger a reduction of the pressure in the anesthetic tank by controlling the pressure reduction unit;
wherein the anesthetic dispenser is selectively operable in an operating mode or in a refill mode, wherein in the operating mode the closure is in the closed position and the control unit maintains an actual pressure in the anesthetic tank at a specified operating pressure or above the specified operating pressure, and in the refill mode the closure is in the open position and the refill opening enables refilling of the at least one anesthetic into the anesthetic tank; and
wherein the control unit is arranged to trigger a reduction of the pressure in the anesthetic tank by controlling the pressure reduction unit such that the actual pressure in the anesthetic tank falls below the operating pressure and remains above an ambient pressure at least in the transition time period and
wherein the control unit is arranged to trigger the pressure reduction after detection of the event that the closure has been moved out of the closed position.

2. An anesthetic dispenser according to claim 1, wherein:
the control unit is configured to reduce the pressure in the anesthetic tank by lowering the actual pressure in the anesthetic tank from the operating pressure to a specified refill pressure which is lower than the operating pressure and higher than the ambient pressure;
wherein the control unit is configured to reduce the pressure after detection of the event that the closure has been moved out of the closed position and
the transition period ends upon the refill pressure being reached.

3. An anesthetic dispenser according to claim 1, further comprising a blocking unit configured to selectively block or allow movement of the closure from the intermediate position to the open position, wherein the anesthetic dispenser is configured such that movement of the closure out of the intermediate position:
is blocked by the blocking unit during the transition time period; and
is enabled by the blocking unit after the transition time period has elapsed.

4. An anesthetic dispenser according to claim 3, wherein the control unit is configured to control the blocking unit in such a way that the blocking unit blocks a movement of the closure out of the intermediate position until the actual pressure in the anesthetic tank has reached a preset refill pressure.

5. An anesthetic dispenser according to claim 1, wherein:
the closure comprises a closure element and a flap;
the closure element is located between the flap and the anesthetic tank and is configured to block the refill opening and be removed out of the refill opening;
the flap is movable between a closed position in which the flap closes the refill opening and an open position in which the flap releases the refill opening; and
the position sensor is configured to detect the event that the flap has been moved out of the closed position.

6. An anesthetic dispenser according to claim 1, further comprising an anesthetic supply unit which is arranged in the anesthetic line guiding from the anesthetic tank to the mixing unit, wherein:
the anesthetic supply unit is configured:
to release the anesthetic line upon the anesthetic dispenser being operated in the operating mode, and during the transition period; and
to feed the at least one anesthetic from the released anesthetic line to the mixing unit; and
the control unit is configured to switch off an anesthetic delivery unit in response to detection of the event that the closure has been moved out of the closed position.

7. An anesthetic dispenser according to claim 1, wherein the controllable pressure reduction unit comprises:
a disposal line leading from the anesthetic tank to a stationary disposal connection or to surroundings; and
a controllable disposal shut-off means configured to selectively shut off or release the disposal line and to be able to shut off the disposal line when the anesthetic dispenser is operated in the operating mode, wherein the control unit is configured to:
control the disposal shut-off means such that the disposal shut-off means releases the disposal line in response to detecting that the closure has been moved out of the closed position; and
control the disposal shut-off means such that the disposal shut-off means shuts off the disposal line after the transition time period has elapsed.

8. An arrangement comprising:
an anesthetic dispenser comprising:
a mixing unit configured to generate a gas mixture comprising at least one anesthetic and a carrier gas;
an anesthetic tank with a refill opening;
a closure for the refill opening, the closure being configured to move from a closed position via an intermediate position to an open position and being configured to close the refill opening in the closed position and in the intermediate position and release the refill opening in the open position;
an anesthetic line leading from the anesthetic tank to the mixing unit;
a controllable pressure increasing unit configured to increase pressure in the anesthetic tank or to effect such a pressure increase;
a controllable pressure reduction unit configured to reduce pressure in the anesthetic tank or to effect such a pressure reduction;
a pressure sensor configured to measure pressure in the anesthetic tank;
a position sensor configured to detect an event that the closure has been moved out of a closed position, wherein the anesthetic dispenser is configured such that a transition time period elapses when the closure is moved from the closed position to the intermediate position; and
a signal processing control unit configured:
to receive measured values from the pressure sensor and the position sensor;
to trigger an increase in pressure in the anesthetic tank by controlling the pressure increasing unit;
to trigger a reduction of the pressure in the anesthetic tank by controlling the pressure reduction unit;
wherein the anesthetic dispenser is selectively operable in an operating mode or in a refill mode, wherein in the operating mode the closure is in the closed position and the control unit maintains an actual pressure in the anesthetic tank at a specified operating pressure or above the specified operating pressure, and in the refill mode the closure is in the open position and the refill opening enables refilling of the at least one anesthetic into the anesthetic tank; and
wherein the control unit is arranged to trigger a reduction of the pressure in the anesthetic tank by controlling the pressure reduction unit such that the actual pressure in the anesthetic tank falls below the operating pressure and remains above an ambient pressure at least in the transition time period,
wherein the control unit is arranged to trigger the pressure reduction after detection of the event that the closure has been moved out of the closed position; and
a carrier gas supply unit in fluid communication with the anesthetic dispenser for supplying the carrier gas, the carrier gas supply unit comprising a carrier gas mixer.

9. A system for anesthetizing a patient, the system comprising:
a ventilator; and
an anesthetic dispenser in fluid communication with the ventilator, wherein the ventilator is configured to anesthetize the patient using a gas mixture generated by the anesthetic dispenser, the anesthetic dispenser comprising:
a mixing unit configured to generate a gas mixture comprising at least one anesthetic and a carrier gas;
an anesthetic tank with a refill opening;
a closure for the refill opening, the closure being configured to move from a closed position via an intermediate position to an open position and being configured to close the refill opening in the closed position and in the intermediate position and release the refill opening in the open position;
an anesthetic line leading from the anesthetic tank to the mixing unit;
a controllable pressure increasing unit configured to increase pressure in the anesthetic tank or to effect such a pressure increase;
a controllable pressure reduction unit configured to reduce pressure in the anesthetic tank or to effect such a pressure reduction;
a pressure sensor configured to measure pressure in the anesthetic tank;
a position sensor configured to detect an event that the closure has been moved out of a closed position, wherein the anesthetic dispenser is configured such that a transition time period elapses when the closure is moved from the closed position to the intermediate position; and a signal processing control unit configured:
to receive measured values from the pressure sensor and the position sensor;
to trigger an increase in pressure in the anesthetic tank by controlling the pressure increasing unit;
to trigger a reduction of the pressure in the anesthetic tank by controlling the pressure reduction unit;
wherein the anesthetic dispenser is selectively operable in an operating mode or in a refill mode, wherein in the operating mode the closure is in the closed position and the control unit maintains an actual pressure in the anesthetic tank at a specified operating pressure or above the specified operating pressure, and in the refill mode the closure is in the open position and the refill opening enables refilling of the at least one anesthetic into the anesthetic tank; and
wherein the control unit is arranged to trigger a reduction of the pressure in the anesthetic tank by controlling the pressure reduction unit such that the actual pressure in the anesthetic tank falls below the operating pressure and remains above an ambient pressure at least in the transition time period, wherein the control unit is arranged to trigger the pressure reduction after detection of the event that the closure has been moved out of the closed position.

10. A system according to claim 9, wherein the ventilator is configured:
to mechanically ventilate the anesthetized patient; and
to generate a maximum ventilation pressure during mechanical ventilation,
wherein the anesthetic dispenser is configured such that the pressure in the anesthetic tank remains above the maximum ventilation pressure in the transition period.

11. A system according to claim 9, further comprising a carrier gas supply unit in fluid communication with the anesthetic dispenser for supplying the carrier gas, the carrier gas supply unit comprising a carrier gas mixer.

12. A process for generating a gas mixture comprising at least an anesthetic and a carrier gas using an anesthetic dispenser comprising a mixing unit, an anesthetic tank with a refill opening, a closure for the refill opening, an anesthetic line guiding from the anesthetic tank to the mixing unit, a controllable pressure increasing unit, a controllable pressure reduction unit, a pressure sensor and a position sensor, the process comprising the step of
measuring an actual pressure in the anesthetic tank with the pressure sensor;
operating the anesthetic dispenser in an operating mode comprising the steps of:
providing the closure in a closed position, in which the closure closes the refill opening;
bringing the actual pressure in the anesthetic tank to a specified operating pressure and/or maintain the pressure equal to or above a specified operating pressure using the pressure increasing unit;
conveying at least one anesthetic from the anesthetic tank through the anesthetic line to the mixing unit; and
generating in the mixing unit a gas mixture comprising anesthetic conveyed to the mixing unit and a carrier gas; and
refilling the anesthetic tank comprising:
moving the closure from the closed position to an open position via an intermediate position, wherein the closure also closes the refill opening in the intermediate position and releases the refill opening in the open position; wherein the closure in the open position allows refilling of the at least one anesthetic into the anesthetic tank; wherein a transition time period occurs during a movement of the closure from the closed position to the intermediate position;
detecting with the position sensor the event that the closure has been moved out of the closed position;
in response to the detection of the event that the closure has been moved out of the closed position lowering by using the pressure reduction unit the actual pressure in the anesthetic tank such that the actual pressure falls below the operating pressure and remains at least in the transition period, above an ambient pressure.

13. A process according to claim 12, wherein:
a refill pressure is specified which is lower than the operating pressure and higher than the ambient pressure; and
the step of lowering the actual pressure in the anesthetic tank is carried such that the pressure is reduced to the specified refill pressure during the transition period; and
the transition period ends when the refill pressure is reached.

* * * * *